US012708737B2

(12) United States Patent
Allmendinger et al.

(10) Patent No.: US 12,708,737 B2
(45) Date of Patent: Aug. 18, 2026

(54) METHOD FOR STRAIGHTENING BENT CATHETERS FOR USE

(71) Applicant: NORTHEAST SCIENTIFIC, INC., Waterbury, CT (US)

(72) Inventors: Craig D. Allmendinger, Waterbury, CT (US); Jeffrey J. Porter, Watertown, CT (US)

(73) Assignee: NORTHEAST SCIENTIFIC, INC., Waterbury, CT (US)

( * ) Notice: Subject to any disclaimer, the term of this patent is extended or adjusted under 35 U.S.C. 154(b) by 1073 days.

(21) Appl. No.: 17/846,905

(22) Filed: Jun. 22, 2022

(65) Prior Publication Data

US 2022/0401692 A1 Dec. 22, 2022

Related U.S. Application Data

(60) Provisional application No. 63/213,422, filed on Jun. 22, 2021.

(51) Int. Cl.
*A61M 25/00* (2006.01)

(52) U.S. Cl.
CPC ..... *A61M 25/00* (2013.01); *A61M 2025/0019* (2013.01); *A61M 2205/0233* (2013.01); *A61M 2205/0266* (2013.01)

(58) Field of Classification Search
CPC .............. A61M 25/00; A61M 25/0009; A61M 2205/0233; A61M 2205/0266; A61M 2025/0019; B29C 73/00
See application file for complete search history.

*Primary Examiner* — Monica A Huson

(74) *Attorney, Agent, or Firm* — McHale & Slavin. P.A.

(57) ABSTRACT

The invention involves a system and method for straightening and refurbishing medical catheters. The system includes the steps and equipment to repair bends and kinks which prevent proper usage of the catheter for a medical procedure. The system and method further checks electrical conductivity and resistance if needed. The catheters are then cleaned and repackaged for shipment and use.

11 Claims, 22 Drawing Sheets

| PROCEDURE TITLE | VNUS KINK REPAIR | | |
|---|---|---|---|
| PROCEDURE # | PI-100066 | REVISION | 02 |

9 KINK REPAIR 40

9.1 TURN ON THE SYSTEM BY PRESSING THE KNOB LOCATED ON THE PANEL ON THE RIGHT SIDE OF THE CAGE.
9.2 SLIDE OPEN THE FRONT OF THE CAGE BY PULLING UP ON THE HANDLE.
9.3 SLIDE THE HEATING ASSEMBLY OUT BY PULLING THE BLACK KNOB TOWARD THE OPERATOR.
9.4 IDENTIFY THE KINK IN THE CATHETER SHEATH.
9.5 GENTLY FLEX THE CATHETER SHEATH TO STRAIGHTEN IT.
9.6 WIPE THE TF-100054 KINK REPAIR SHORT WIRE (.025in x 27in) AND TF-100055 KINK REPAIR LONG WIRE (.025in x 52in) WITH A CS-100001 LINT-FREE WIPES (9'x9") AND CS-100011 70% ETHYL ALCOHOL BETWEEN EACH LOT IT IS USED.
9.7 WIPE BOTH HALVES OF THE TF-100010 VNUS KINK REPAIRER MOLD WITH CS-100001 LINT-FREE WIPES (9'x9") AND CS-100011 70% EHTYL ALCOHOL IF THEY APPEAR UNCLEAN.
9.7.1 PRIOR TO USING THE MOLD, OBSERVE IT FOR ANY CRACKS, CHIPS OR MAJOR DISCOLORATION. IF THERE ARE ANY CRACKS, CHIPS OR MAJOR DISCOLORATIONS, NOTIFY THE PRODUCTION MANAGER AND WAIT TO PROCEED UNTIL A NEW MOLD CAN BE USED.
9.8 STARTING AT THE DISTAL END OF THE DEVICE, SLOWLY PUSH THE GUIDEWIRE (TF-100054 OR TF-100055) THROUGH THE LUMEN UNTIL THE GUIDEWIRE EMERGES FROM THE LUER END OF THE DEVICE.
9.8.1 WATCH THE GUIDEWIRE EMERGE THROUGH THE LUER PORT TO ENSURE THAT NO DEBRIS CAME OUT OF THE LUMEN. IF ANY DEBRIS COMES OUT OF THE LUMEN IT IS CONSIDERED ROUTINE SCRAP AND MUST BE MARKED ON THE TRAVELER AS A REJECT.
9.9 PLACE THE KINKED SHEATH INTO THE GROOVE OF ONE OF THE MOLD HALVES SO THE KINK IS AT THE CENTER OF THE MOLD.
9.10 PLACE THE OTHER MOLD HALF ON TOP SO THE TWO MOLD HALVES ENVELOPE THE SHEATH.
9.11 ENSURE THAT THE MOLD CLOSES AROUND THE SHEATH SO THERE ARE NO GAPS BETWEEN THE MOLD HALVES.
9.12 PLACE A CLAMPING CLIP ON THE LEFT END OF THE ENTIRE MOLD, CLAMPING BOTH HALVES TOGETHER.
9.13 PLACE A THE DEVICE HANDLE AND CABLE BUNDLE ON THE MENTAL STAGE AT THE LEFT OF THE CAGE.
9.14 FEED THE CATHETER THROUGH THE HEATING COIL AND INSERT THE MOLD INTO THE HEATER COIL SO THE MOLD ENTERS FROM LEFT TO RIGHT.
9.15 INSERT THE MOLD UNTIL THE RIGHT END OF THE MOLD PROTRUDES FROM THE HEATING COIL.
9.16 WHEN THE RIGHT END OF THE MOLD CLEARS THE HEATING COIL, CLAMP IT WITH THE METAL CLIP.
9.17 SLIDE THE HEATING ASSEMBLY BACK INTO THE CAGE UNTIL HITS THE STOP.
9.18 CLOSE THE FRONT DOOR OF THE CAGE.
9.19 PUSH THE GREEN BUTTON TO THE RIGHT OF THE CAGE DOOR IN ORDER TO START THE HEATING/COOLING CYCLE.
9.20 THE END OF THE HEATING/COOLING CYCLE WILL BE IDENTIFIED WHEN THE AIR CEASES TO BLOW.
9.20.1 PRIOR TO REMOVING THE MOLD, ENSURE THE TEMPERATURE OF THE HEATING COIL IS BELOW 85°F, AS INDICATED ON THE PANEL TO THE RIGHT.

| PROCEDURE TITLE | VNUS KINK REPAIR | | |
|---|---|---|---|
| PROCEDURE # | PI-100066 | REVISION | 02 |

10

OVERVIEW

14

| PARTS AND DOCUMENTS | |
|---|---|
| NUMBER | DESCRIPTION |
| R-CF7-3-60 | NES REPROCESSED CATHETER |
| R-CF7-7-60 | NES REPROCESSED CATHETER |
| R-CF7-7-100 | NES REPROCESSED CATHETER |
| CS-100001 | LINT-FREE WIPES (9x9") |
| CS-100011 | 70% ETHYL ALCOHOL |
| MAT-100077 | LOCTITE 4011 |
| T-1003 | VNUS TRAVELER |

16, 12

| EQUIPMENT | |
|---|---|
| NUMBER | DESCRIPTION |
| EQ-1039 | VNUS KINK REPAIRER |
| EQ-1058 | VNUS KINK REPAIRER |
| EQ-1064 | VNUS COLLAR REMOVER |
| TF-100010 | VNUS KINK REPAIR MOLD |
| TF-100054 | KINK REPAIR SHORT WIRE (.025in x 29in) |
| TF-100055 | KINK REPAIR LONG WIRE (.025in x 52in) |

SETUP AND PROCEDURE

18

| STEP | VARIABLE |
|---|---|
| EQ-1064 | COLLAR REMOVAL |
| EQ-1039, EQ-1058 | KINK REPAIRER |
| MAT-100077 | COLLAR ATTACHMENT |

20

INSPECTION

| SAMPLE SIZE | ACCEPTANCE CRITERIA | METHOD |
|---|---|---|
| 100% | KINK WAS REPAIRED | VISUAL, UNAIDED EYE 12-18" AWAY |
| 100% | NO COLLAR DAMAGE | VISUAL, UNAIDED EYE 12-18" AWAY |

FIG. 1

| PROCEDURE TITLE | VNUS KINK REPAIR | | |
|---|---|---|---|
| PROCEDURE # | PI-100066 | REVISION | 02 |

1 PURPOSE

THE PURPOSE OF THIS PROCESS INSTRUCTION IS TO DETAIL HOW THE R-CF7-3-60 NES REPROCESSED SD-CF7-3-60 CATHETER, R-CF7-7-60 NES REPROCESSED SD-CF7-7-60 CATHETER, AND R-CF7-7-100 NES REPROCESSED SD-CF7-7-100 CATHETER (VNUS) DEVICES ARE KINK REPAIRED.

2 SCOPE

THIS PROCESS INSTRUCTION APPLIES TO KINK REPAIR FOR VNUS DEVICES.

| PROCEDURE TITLE | VNUS KINK REPAIR | | |
| --- | --- | --- | --- |
| PROCEDURE # | PI-100066 | REVISION | 02 |

| PROCEDURE TITLE | VNUS KINK REPAIR | | |
|---|---|---|---|
| PROCEDURE # | PI-100066 | REVISION | 02 |

4 EQUIPMENT, MATERIAL AND DOCUMENTS 4.1 MATERIAL LIST

26

| PART NUMBER | DESCRIPTION |
|---|---|
| MAT-100077 | LOCTITE 4011 |
| CS-100001 | LINT-FREE WIPES (9x9") |
| CS-100011 | 70% ETHYL ALCOHOL |

4.2 EQUIPMENT AND TOOLING LIST

28

| EQUIPMENT NUMBER | DESCRIPTION |
|---|---|
| KRS1* | KINK REPAIR WORKSTATION |
| EQ-1039 | VNUS KINK REPAIRER |
| EQ-1058 | VNUS KINK REPAIRER |
| EQ-1064 | VNUS COLLAR REMOVER |
| TF-100010 | VNUS KINK REPAIR MOLD |
| TF-100054 | KINK REPAIR SHORT WIRE (.025in x 29in) |
| TF-100055 | KINK REPAIR LONG WIRE (.025in x 52in) |

*EQUIVALENT ACCEPTABLE 4.3 DOCUMENTS

30

| DOCUMENT NUMBER | DESCRIPTION |
|---|---|
| T-1003 | VNUS TRAVELER |
| SOP-100012* | PRODUCTION AND PROCESS CONTROL |
| SOP-100015* | NON-CONFORMING PRODUCT |
| SOP-100021* | GOOD DOCUMENTATION PRACTICES |
| SOP-100029* | GOOD MANUFACTURING PRACTICES |

*REFERENCE DOCUMENTS ONLY

5 CLEAN ROOM ENTRY 5.1 ENTER THE CLEAN ROOM FOLLOWING WI-100014.

FIG. 4

| PROCEDURE TITLE | VNUS KINK REPAIR | | |
|---|---|---|---|
| PROCEDURE # | PI-100066 | REVISION | 02 |

32

6 LINE CLEARANCE & DOCUMENTATION REVIEW 6.1 VERIFY YOU HAVE BEEN SIGNED OFF ON THE TRAINING RECORD FOR THIS PI. IF YOU HAVE NOT BEEN SIGNED OFF AS BEING TRAINED, NOTIFY THE PRODUCTION SUPERVISOR.

6.2 REVIEW THE TRAVELER TO ENSURE ALL PRIOR PROCESS STEPS WERE COMPLETED. IF THE PRIOR STEPS WERE NOT COMPLETED, CONTACT THE PRODUCTION SUPERVISOR.

6.3 VERIFY THAT LINE CLEARANCE HAS BEEN COMPLETED. IF NOT, PERFORM LINE CLEARANCE PER SOP-100029.

6.4 ALL TECHNICIANS WHO VERIFY AND PERFORM THE LINE CLEARANCE PROCESS MUST SIGN OFF ON THE TRAVELER.

7 SET-UP

34

7.1 DETERMINE IF THE DEVICE NEEDS KINK REPAIR OR KINK IN THE COLLAR REPAIR:

BLUE - ELEMENT REPAIR
YELLOW - KINK REPAIR
RED - KINK IN THE COLLAR REPAIR 35, 37

7.2 IF THE DEVICE NEEDS KINK IN THE COLLAR REPAIR SECTION 8-10 WILL BE FOLLOWED.

7.3 IF THE DEVICE NEEDS ONLY KINK REPAIR ONLY SECTION 9 WILL BE COMPLETED.

38

8 COLLAR REMOVAL

36

8.1 PLACE THE VNUS DEVICE IN THE HOLDER OF EQ-1064 WITH THE WHITE BELLY OF THE HANDLE FACING THE OPERATOR.

8.2 SLIDE THE SHEATH OF THE DEVICE UP THROUGH THE PLASTIC TUBING.

8.3 SECURE THE DEVICE BY LOCKING THE HANDLE IN PLACE WITH THE LOCKING MECHANISM. ENSURE THE DEVICE IS PROPERLY ALIGNED IN THE DEVICE HOLDER.

8.4 TURN ON THE SYSTEM BY TURNING THE KNOB TO THE “ON” POSITION.

8.5 ENSURING YOUR HANDS ARE AWAY FROM THE MACHINE, STEP DOWN ON THE PEDAL AND HOLD THE PEDAL UNTIL THE DEVICE HANDLE MAKES ONE AND A HALF ROTATIONS AGAINST THE RAZOR.

8.6 CAREFULLY REMOVE THE DEVICE FROM THE HOLDER AND PLASTIC TUBING.

8.7 GENTLY TWIST THE RUBBER COLLAR IN BOTH DIRECTIONS TO CLEARLY FREE IT FROM THE VNUS PLASTIC HUB AND SLIDE IT DOWN TOWARDS THE DISTAL END (ELEMENT).

8.8 REMOVE THE RESIDUAL COLLAR MATERIAL FROM THE COLLAR NECK USING A RAZOR. USE CAUTION TO AVOID SCORING THE PLASTIC WHILE SCRAPING THE COLLAR MATERIAL.

FIG. 5

| PROCEDURE TITLE | VNUS KINK REPAIR | | |
|---|---|---|---|
| PROCEDURE # | PI-100066 | REVISION | 02 |

9 KINK REPAIR

40

9.1 TURN ON THE SYSTEM BY PRESSING THE KNOB LOCATED ON THE PANEL ON THE RIGHT SIDE OF THE CAGE.

9.2 SLIDE OPEN THE FRONT OF THE CAGE BY PULLING UP ON THE HANDLE.

9.3 SLIDE THE HEATING ASSEMBLY OUT BY PULLING THE BLACK KNOB TOWARD THE OPERATOR.

9.4 IDENTIFY THE KINK IN THE CATHETER SHEATH.

9.5 GENTLY FLEX THE CATHETER SHEATH TO STRAIGHTEN IT.

9.6 WIPE THE TF-100054 KINK REPAIR SHORT WIRE (.025in x 27in) AND TF-100055 KINK REPAIR LONG WIRE (.025in x 52in) WITH A CS-100001 LINT-FREE WIPES (9'x9") AND CS-100011 70% ETHYL ALCOHOL BETWEEN EACH LOT IT IS USED.

9.7 WIPE BOTH HALVES OF THE TF-100010 VNUS KINK REPAIRER MOLD WITH CS-100001 LINT-FREE WIPES (9'x9") AND CS-100011 70% EHTYL ALCOHOL IF THEY APPEAR UNCLEAN.

9.7.1 PRIOR TO USING THE MOLD, OBSERVE IT FOR ANY CRACKS, CHIPS OR MAJOR DISCOLORATION. IF THERE ARE ANY CRACKS, CHIPS OR MAJOR DISCOLORATIONS, NOTIFY THE PRODUCTION MANAGER AND WAIT TO PROCEED UNTIL A NEW MOLD CAN BE USED.

9.8 STARTING AT THE DISTAL END OF THE DEVICE, SLOWLY PUSH THE GUIDEWIRE (TF-100054 OR TF-100055) THROUGH THE LUMEN UNTIL THE GUIDEWIRE EMERGES FROM THE LUER END OF THE DEVICE.

9.8.1 WATCH THE GUIDEWIRE EMERGE THROUGH THE LUER PORT TO ENSURE THAT NO DEBRIS CAME OUT OF THE LUMEN. IF ANY DEBRIS COMES OUT OF THE LUMEN IT IS CONSIDERED ROUTINE SCRAP AND MUST BE MARKED ON THE TRAVELER AS A REJECT.

9.9 PLACE THE KINKED SHEATH INTO THE GROOVE OF ONE OF THE MOLD HALVES SO THE KINK IS AT THE CENTER OF THE MOLD.

9.10 PLACE THE OTHER MOLD HALF ON TOP SO THE TWO MOLD HALVES ENVELOPE THE SHEATH.

9.11 ENSURE THAT THE MOLD CLOSES AROUND THE SHEATH SO THERE ARE NO GAPS BETWEEN THE MOLD HALVES.

9.12 PLACE A CLAMPING CLIP ON THE LEFT END OF THE ENTIRE MOLD, CLAMPING BOTH HALVES TOGETHER.

9.13 PLACE A THE DEVICE HANDLE AND CABLE BUNDLE ON THE MENTAL STAGE AT THE LEFT OF THE CAGE.

9.14 FEED THE CATHETER THROUGH THE HEATING COIL AND INSERT THE MOLD INTO THE HEATER COIL SO THE MOLD ENTERS FROM LEFT TO RIGHT.

9.15 INSERT THE MOLD UNTIL THE RIGHT END OF THE MOLD PROTRUDES FROM THE HEATING COIL.

9.16 WHEN THE RIGHT END OF THE MOLD CLEARS THE HEATING COIL, CLAMP IT WITH THE METAL CLIP.

9.17 SLIDE THE HEATING ASSEMBLY BACK INTO THE CAGE UNTIL HITS THE STOP.

9.18 CLOSE THE FRONT DOOR OF THE CAGE.

9.19 PUSH THE GREEN BUTTON TO THE RIGHT OF THE CAGE DOOR IN ORDER TO START THE HEATING/COOLING CYCLE.

9.20 THE END OF THE HEATING/COOLING CYCLE WILL BE IDENTIFIED WHEN THE AIR CEASES TO BLOW.

9.20.1 PRIOR TO REMOVING THE MOLD, ENSURE THE TEMPERATURE OF THE HEATING COIL IS BELOW 85°F, AS INDICATED ON THE PANEL TO THE RIGHT.

FIG. 6

| PROCEDURE TITLE | VNUS KINK REPAIR | | |
|---|---|---|---|
| PROCEDURE # | PI-100066 | REVISION | 02 |

9.21 LIFT THE FRONT OF THE CAGE.
9.22 SLIDE THE HEATING ASSEMBLY OUT BY PULLING THE BLACK KNOB TOWARD THE OPERATOR.
9.23 REMOVE THE CLIP FROM THE RIGHT SIDE OF THE MOLD.
9.24 SLIDE THE MOLD CONTAINING THE DEVICE SHEATH FROM THE HEATER RIGHT TO LEFT.
9.25 REMOVE THE LEFT-HAND CLIP WHICH RELEASES THE TWO MOLD HALVES FROM THE SHEATH.
9.26 SEPARATE THE MOLD HALVES AND REMOVE THE CATHETER SHEATH.
9.27 REMOVE THE GUIDEWIRE FROM THE LUMEN OF THE DEVICE.
9.28 INSPECT THE KINKED AREA TO ENSURE IT IS REPAIRED.
9.29 REPEAT STEPS 9.9-9.28 FOR ALL KINKS IN THE DEVICE.
9.30 PERFORM IN-PROCESS INSPECTION PER SECTION 11.

10 COLLAR ATTACHMENT 10.1 ONCE THE KINK HAS BEEN REPAIRED, SLIDE THE COLLAR BACK TOWARDS THE HANDLE.
10.2 USING MAT-100077 LOCTITE 4011, PLACE A 360° LINE OF GLUE AROUND THE TIP OF THE HANDLE NECK WHERE THE COLLAR BASE HAD BEEN PLACED.
10.3 ONCE THE GLUE LINE HAS BEEN PLACED AROUND THE HANDLE NECK, IMMEDIATELY SLIDE THE COLLAR BACK ONTO THE HANDLE NECK SO THE BASE OF THE COLLAR COVERS THE BASE OF THE HANDLE NECK.
10.4 HOLD THE COLLAR IN PLACE FOR AT LEAST 30 SECONDS.
10.5 ENSURE THE BASE OF THE COLLAR IS COMPLETELY SEALED WITH GLUE. IF IT IS NOT. THEN PLACE A SMALL BEAD OF GLUE AROUND THE BASE OF THE COLLAR SO A SEAL IS CREATED.
10.6 REMOVE ANY EXCESS MAT-100077 LOCTITE 4011 WITH A CS-100001 LINT-FREE WIPES (9'x9").
10.7 PERFORM IN-PROCESS INSPECTION PER SECTION 11
10.8 ALL TECHNICIANS WHO PERFORM POUCH SEALING MUST SIGN OFF ON THE TRAVELER.

FIG. 7

| PROCEDURE TITLE | VNUS KINK REPAIR | | |
|---|---|---|---|
| PROCEDURE # | PI-100066 | REVISION | 02 |

11 IN-PROCESS INSPECTIONS 11.1 FOR NON-CONFORMANCES LABELED AS ROUTINE SCRAP, AN NCR DOES NOT NEED TO BE GENERATED PER SOP-100015.

11.2 IF THE NON-CONFORMANCE IS NOT ROUTINE SCRAP, CONTACT QUALITY. AN NCR SHALL BE GENERATED PER SOP-100015.

| SECTION # | SAMPLE SIZE | ACCEPTANCE CRITERIA | METHOD | EXCEPTIONS | REWORK? | ROUTINE SCRAP? |
|---|---|---|---|---|---|---|
| SECTION 9 | 100% | KINK WAS REPAIRED | VISUAL, UNAIDED EYE 12-18" AWAY | N/A | NO | YES |
| SECTION 10 | 100% | NO COLLAR DAMAGE | VISUAL, UNAIDED EYE 12-18" AWAY | N/A | NO | YES |

12 REVISION HISTORY

| REVISION | CR NUMBER | CHANGES MADE |
|---|---|---|
| 01 | SEE MASTER CONTROL | INITIAL RELEASE. ADAPTED FROM RP-1099 |
| 02 | SEE MASTER CONTROL | ADDED OVERVIEW PAGE. UPDATED IP-1107 TO INP-100027 ON FLOW CHART. |

FIG. 8

METHOD FOR STRAIGHTENING BENT CATHETERS FOR USE

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 63/213,422, entitled "METHOD FOR STRAIGHTENING BENT CATHETERS FOR USE", filed Jun. 22, 2021. The contents of the above referenced application are incorporated herein by reference in their entirety.

FIELD OF INVENTION

The present invention generally relates to medical catheters; and more particularly, to a method of straightening catheters that have been bent or kinked due to shipping or handling issues during use.

BACKGROUND INFORMATION

In order to reach locations within the human anatomy or vascular system, guide catheters are commonly used. Most guide catheters have proximal and distal ends connected by a long, tubular body having one or more lumens formed therein. The proximal end of the catheter usually includes a handle for control of the catheter by the operator and various ports for introduction of fluids and instruments through the catheter lumen. The distal end includes a tip which is inserted into the patient. For example, in vascular applications, the tip of the catheter can be inserted into a major vein, artery, or other body cavity. The catheter is then further inserted and guided to the area of concern. Moreover, the catheter can also function as a "sheath" or "guide catheter" in that it can be used as a delivery conduit for other tools, such as balloons and/or stents for performing angioplasty, or other instruments mapping electrodes and ablation devices for conducting procedures within the human anatomy.

Current methods for inserting and guiding a catheter include the use of a guide wire, where the guide wire is fed into position within the patient and then the catheter is passed over the guide wire. However, one drawback associated with this method, when the target ablation sites are in or near the pulmonary veins on the posterior surface of the heart, is that it is often difficult, if not impossible, to advance the guide wire all the way to the ultimate target site due to the shape of the heart muscle.

Alternatively, a steerable catheter can be used. Steerable catheters require an ability to selectively deflect the distal tip of the catheter in a desired direction by permitting an operator to adjust the direction of advancement of the distal end of the catheter, as well as to position the distal portion of the catheter. The deflection of the distal tip is typically provided by one or more pull wires that are attached at the distal end of the catheter and extend to a control handle such that the surgeon can selectively deflect the tip and/or rotate the catheter shaft to navigate into the correct position.

When designing such steerable catheters for access into the heart, it is important to have sufficient flexibility in the catheter shaft so that when the catheter is advanced through a blood vessel or heart chamber it can follow the inherent curvature of the biological structures without puncturing them. However, achieving a balance between the "pushability" of the catheter (that is, the ability to direct the tip of the catheter to the target location without buckling or kinking) and the necessary stiffness to allow the catheter to access areas of the anatomy, especially when navigating the sharp turns necessary to access locations in the left atrium of the heart, can be difficult.

More difficulties arise when the catheter includes an ablation instrument having a balloon, as additional maneuvering can be required to properly orient the balloon within or at the mouth of the vein. Further, axial force may be required in order to occlude the pulmonary vein at the ostium, and the lack of stiffness of most catheters renders the application of sufficient force to successfully seal the vein prior to ablation problematic.

These drawbacks often result in bent and/or kinked catheter sheathing. Once bent, the catheter must be replaced, adding significant costs to the surgical procedure. The bent catheters are then typically disposed of.

Therefore, there exists a need in the art to refurbish these bent and/or kinked catheters so that they can be used or re-used to complete surgical procedures. The method of straightening the catheters should be relatively quick and require a minimal amount of tools and hardware. The method and system should not require excessive strength to straighten and check the catheters. Still, the system and method should straighten the catheters in such a way so as not to detract from the aesthetic appearance of the refurbished catheter.

Thus, the present invention provides a method and system for straightening and refurbishing medical catheters which overcomes the disadvantages of prior art. The method and system for straightening catheters of the present invention not only provides for relative ease in the steps and procedures, it also permits a catheter to be used or re-used in surgical procedure.

SUMMARY OF THE INVENTION

Briefly, the invention involves a system and method for straightening and refurbishing medical catheters. The system includes the steps and equipment to repair bends and kinks which prevent proper usage of the catheter for a medical procedure. The system and method further checks electrical conductivity and resistance if needed. The catheters are then cleaned and repackaged for shipment and use.

Accordingly, it is an objective of the present invention to provide a system and method of repairing and/or refurbishing medical catheters.

It is a further objective of the present invention to provide a multi-step system and method for repairing and/or refurbishing medical catheters.

It is yet a further objective of the present invention to provide a series of equipment suitable for use with the method and system for repairing medical catheters.

Other objectives and advantages of this invention will become apparent from the following description taken in conjunction with the accompanying drawings wherein are set forth, by way of illustration and example, certain embodiments of this invention. The drawings constitute a part of this specification, include exemplary embodiments of the present invention, and illustrate various objects and features thereof.

BRIEF DESCRIPTION OF THE FIGURES

FIG. 1 is an overview of a method and system procedure for repairing a medical catheter;

FIG. 4 is an example of equipment, material and documents needed for repairing medical catheters;

FIG. 5 outlines a portion of the system and method used for straightening a medical catheter;

FIG. 6 outlines a portion of the system and method used for straightening a medical catheter;

FIG. 7 outlines a portion of the system and method used for straightening a medical catheter;

FIG. 8 outlines a portion of the system and method used for straightening a medical catheter;

DETAILED DESCRIPTION OF THE PREFERRED EMBODIMENTS

Figure 2:
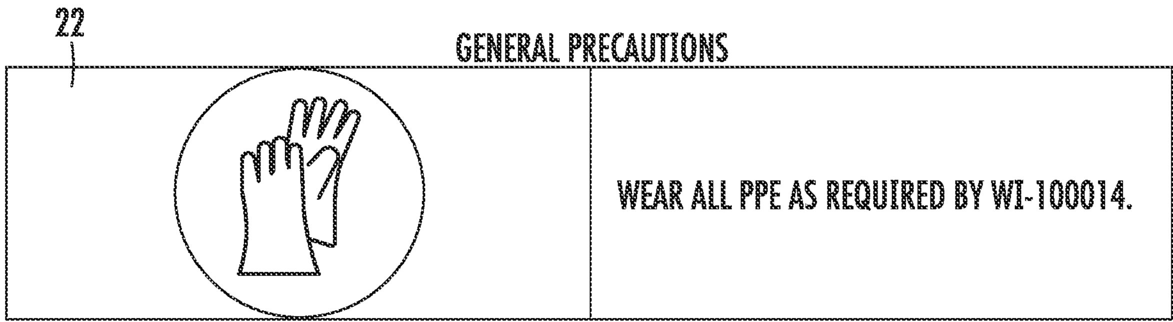
FIG. 2 is a list of precautions suitable for use with the present system and method.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Figure 3:
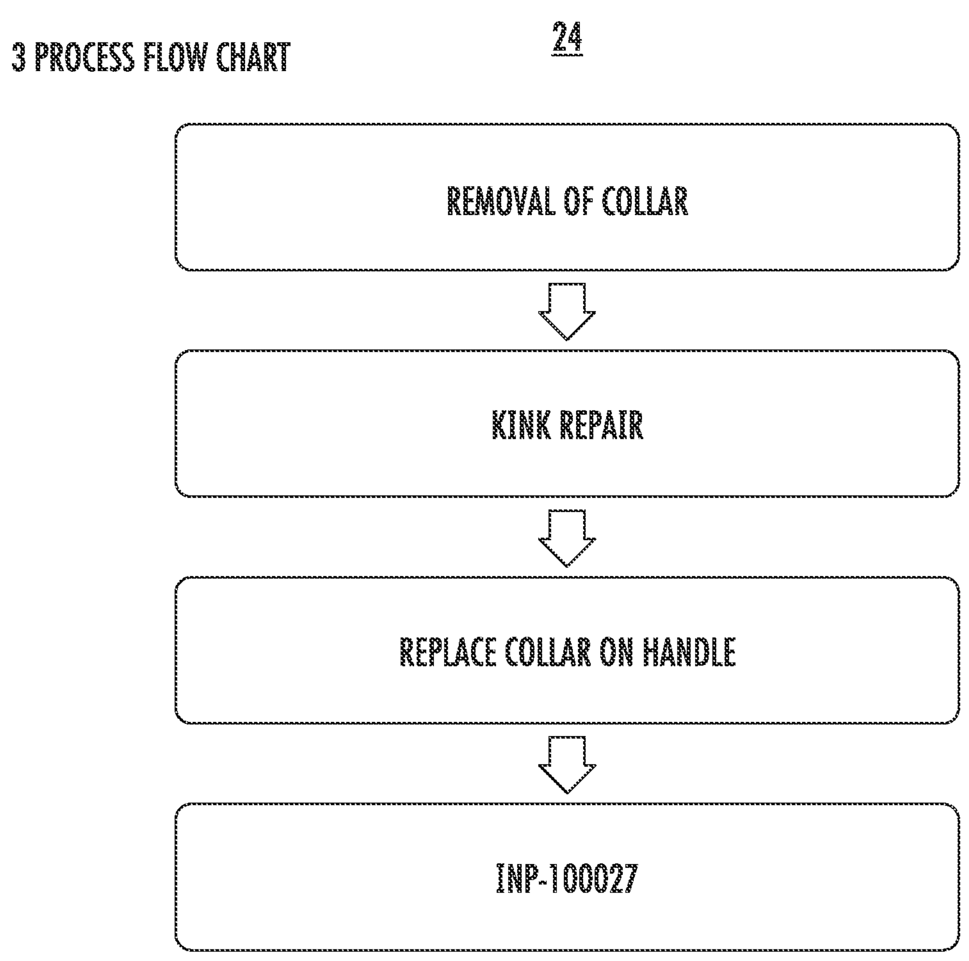
FIG. 3 is a flow chart illustrating one embodiment of steps utilized in the procedure for repairing a kinked or bent medical catheter.
Figure 9:
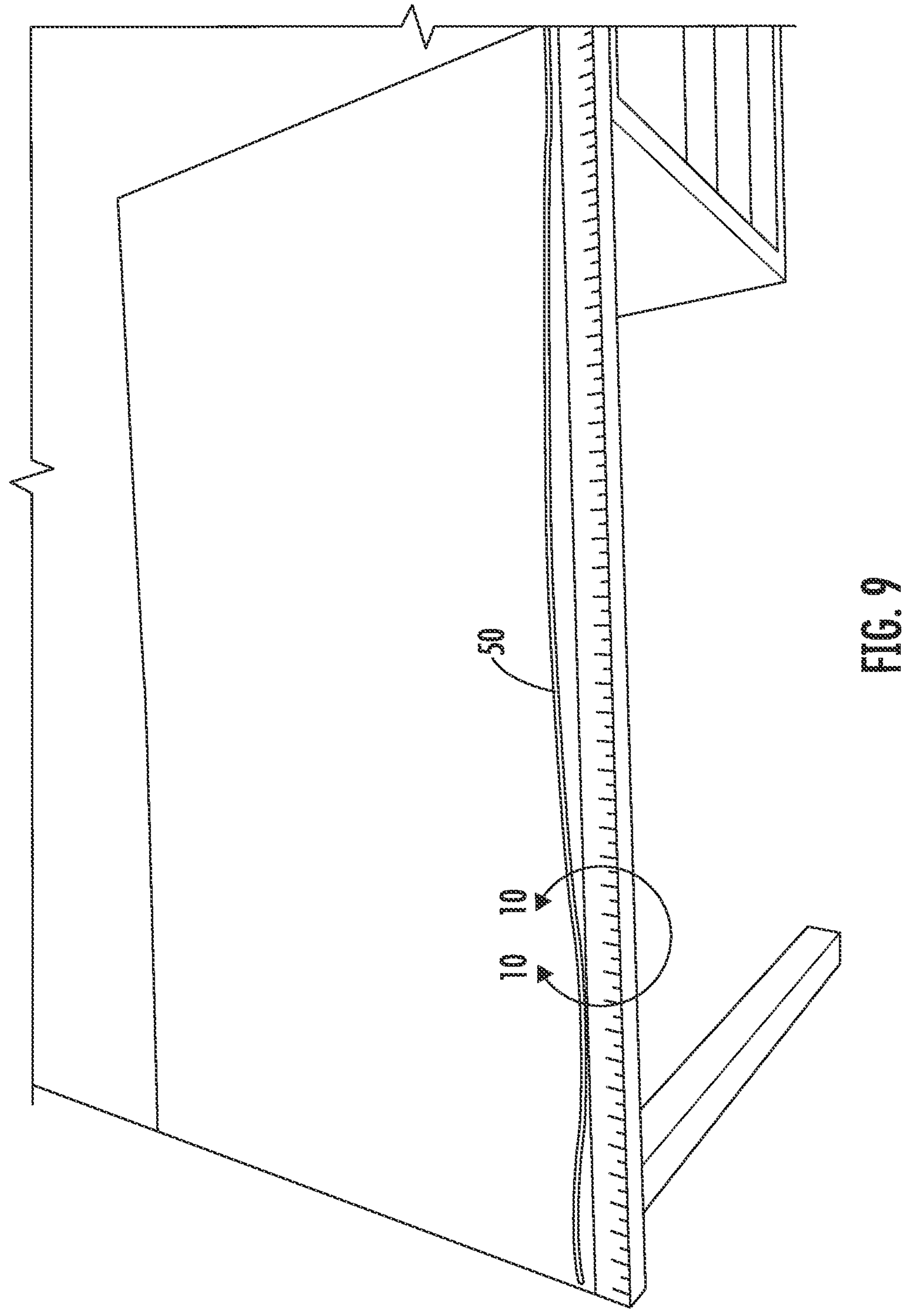
FIG. 9 illustrates the initial examination of the medical catheter.
Figure 10:
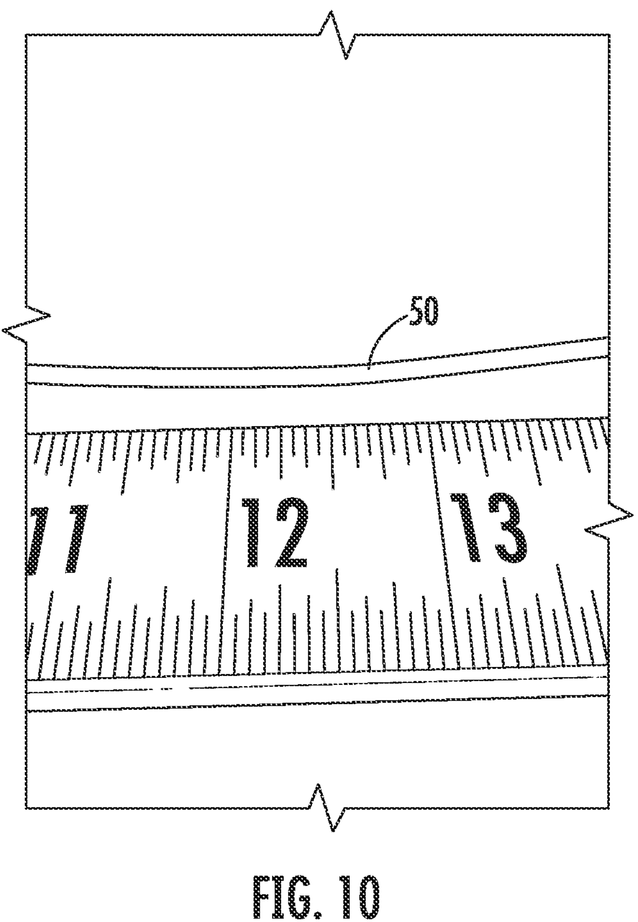
FIG. 10 is a partial view, taken along lines 10-10 of FIG. 9, illustrating a bent or kinked portion of a medical catheter.
Figure 11:
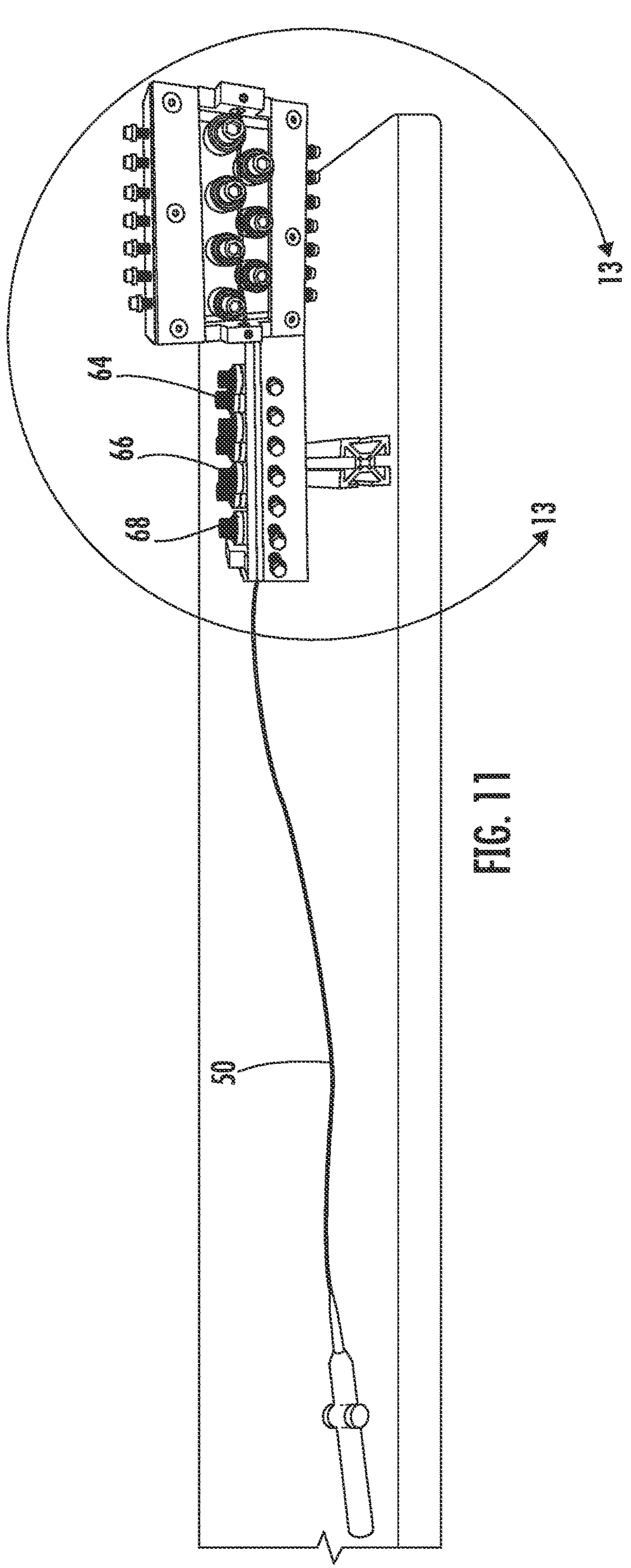
FIG. 11 illustrates a portion of the straightening method utilizing a roll straightener.
Figure 12:
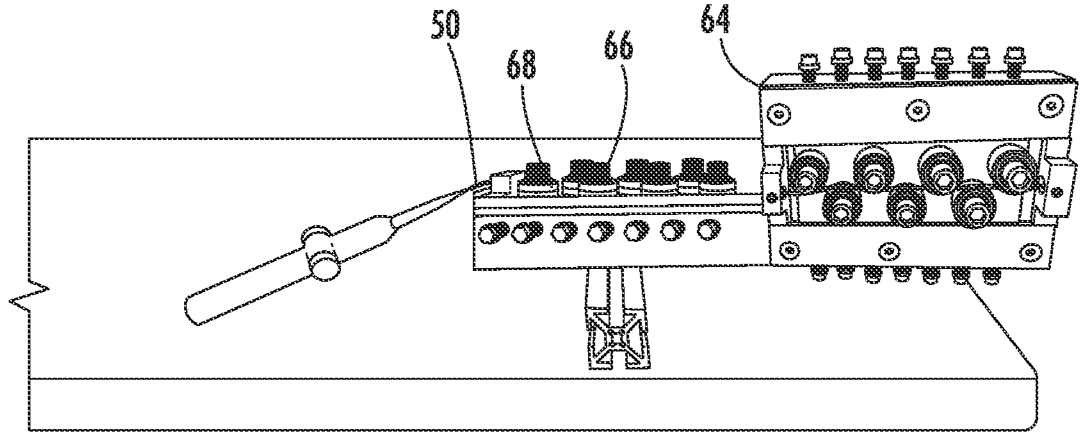
FIG. 12 illustrates a portion of the straightening method utilizing a roll straightener.
Figure 13:
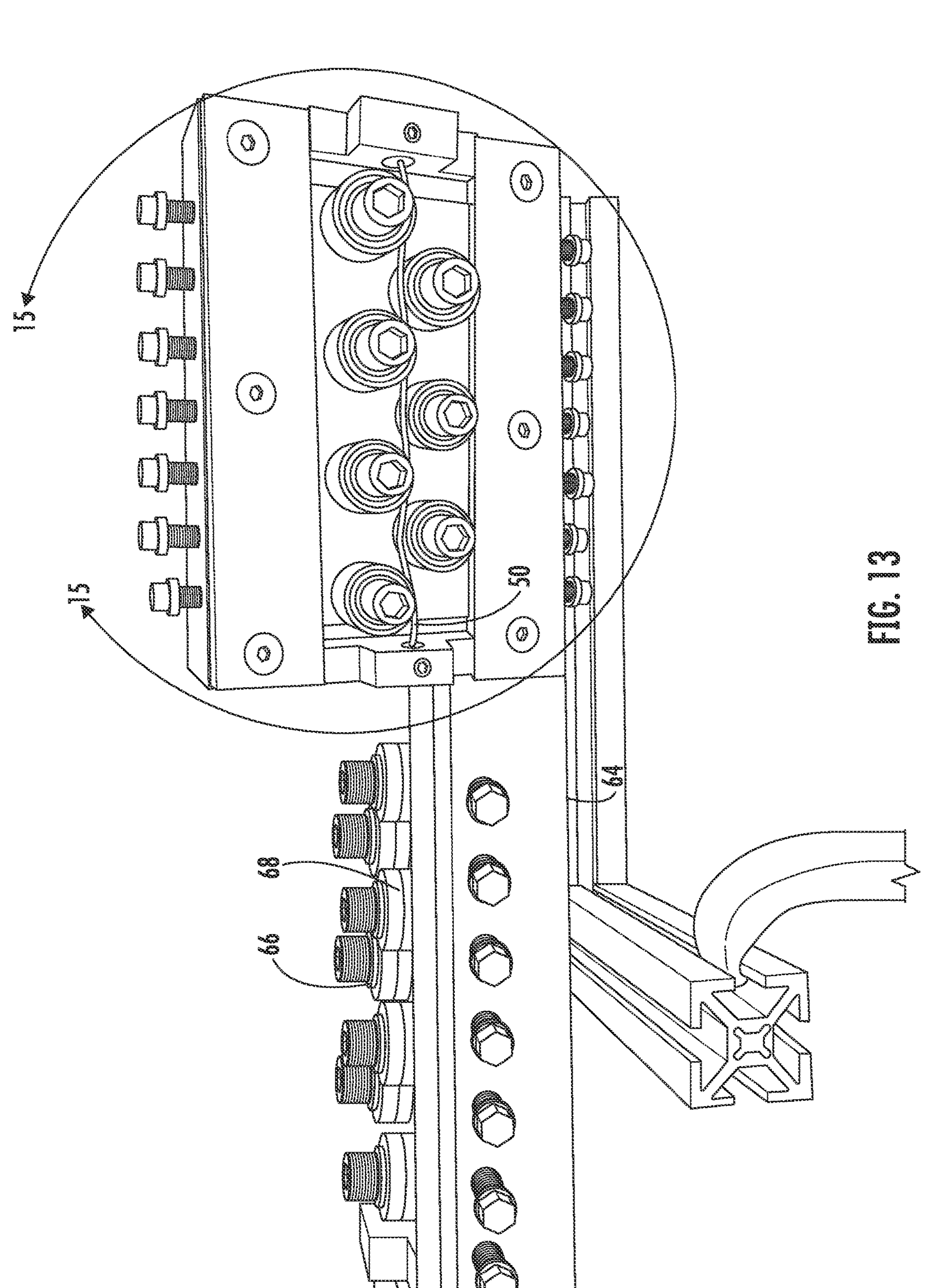
FIG. 13 is a partial view taken along lines 13-13 of FIG. 11 illustrating the roll straightener cooperating with the catheter.
Figure 14:
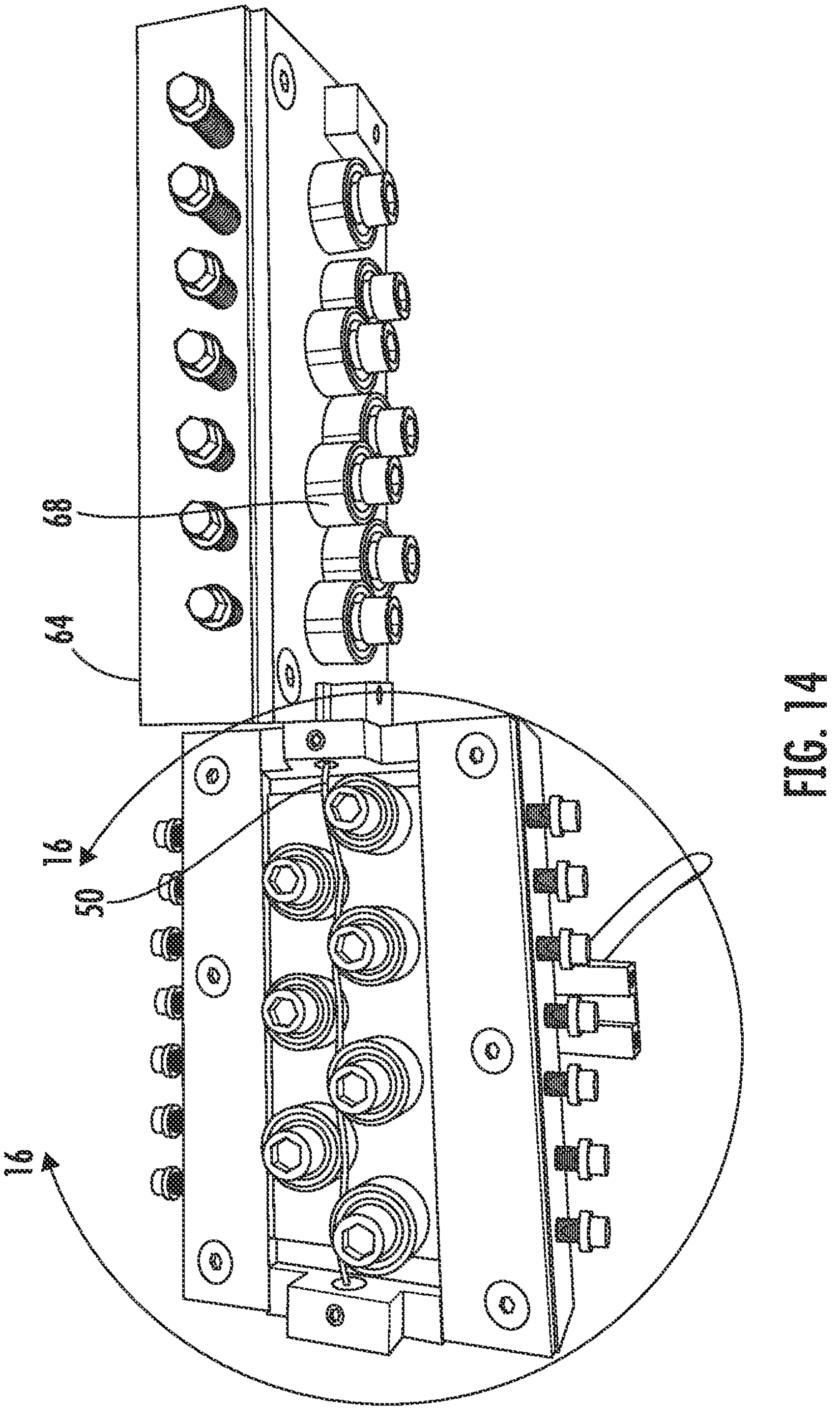
FIG. 14 is a top view illustrating the roll straightener cooperating with the catheter.
Figure 15:
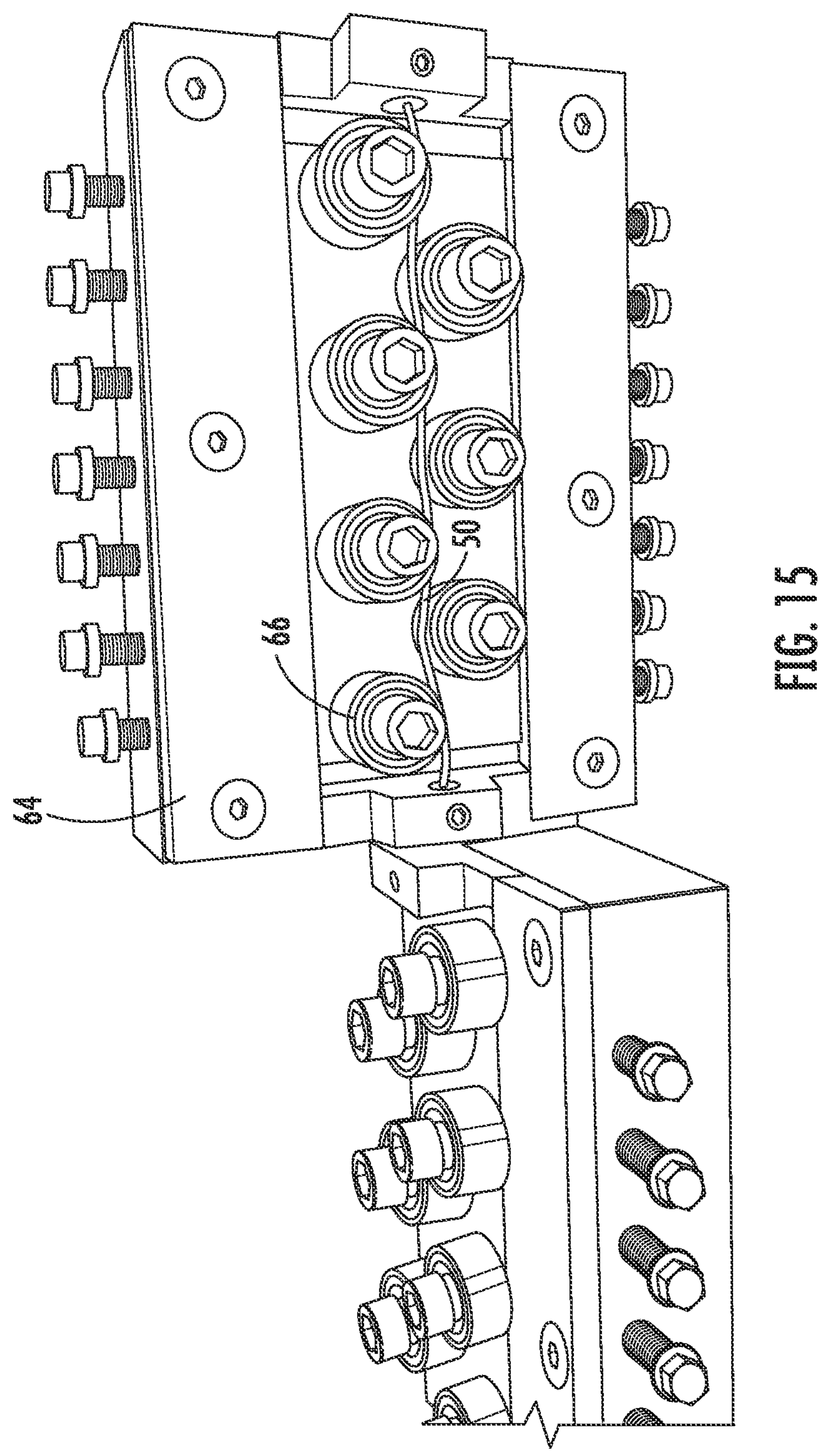
FIG. 15 is a partial view, taken along lines 15-15 of FIG. 13, illustrating the roll straightener cooperating with the catheter.
Figure 16:
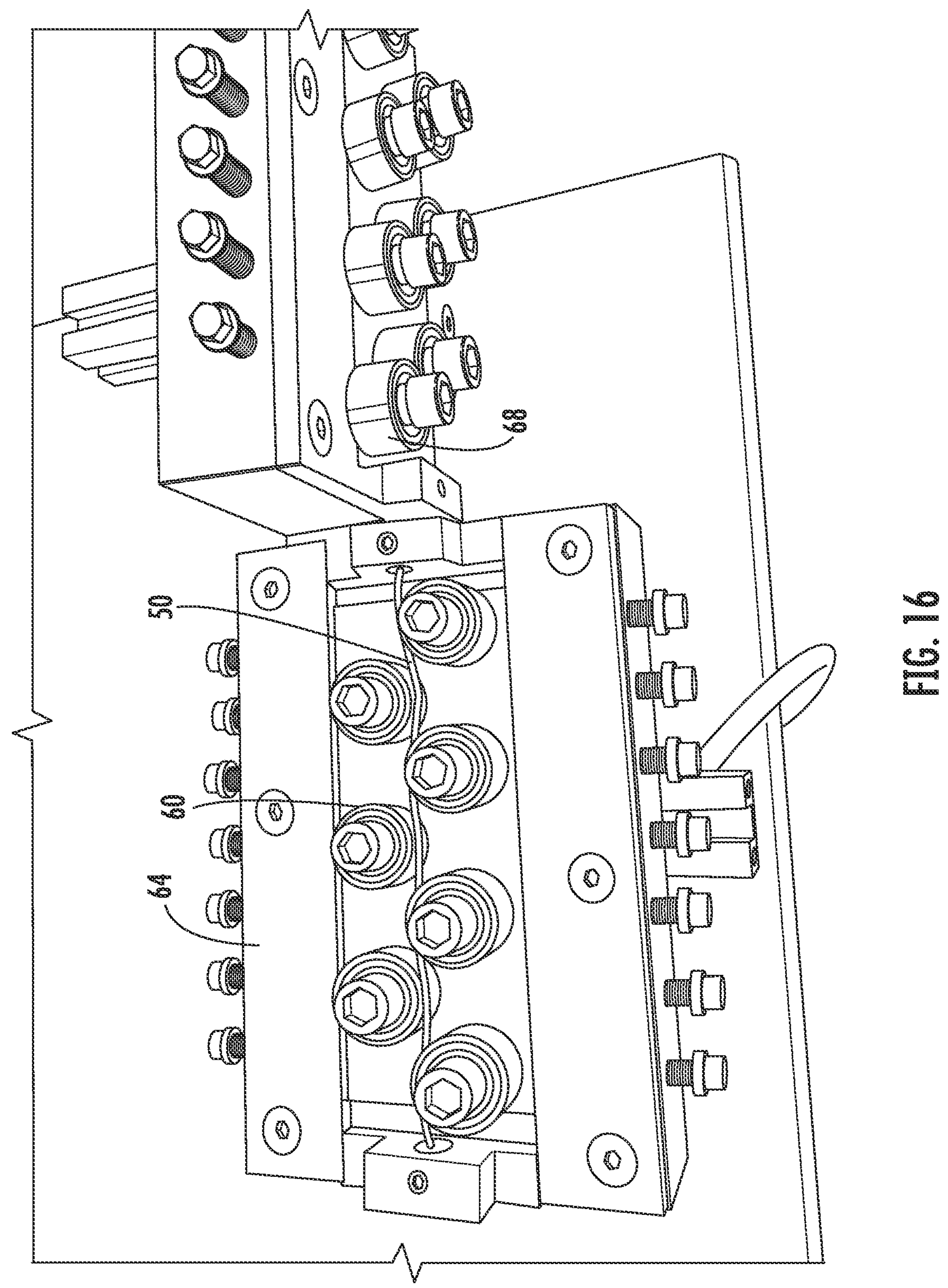
FIG. 16 is a partial view, taken along lines 16-16 of FIG. 14, illustrating the roll straightener cooperating with the catheter.
Figure 17:
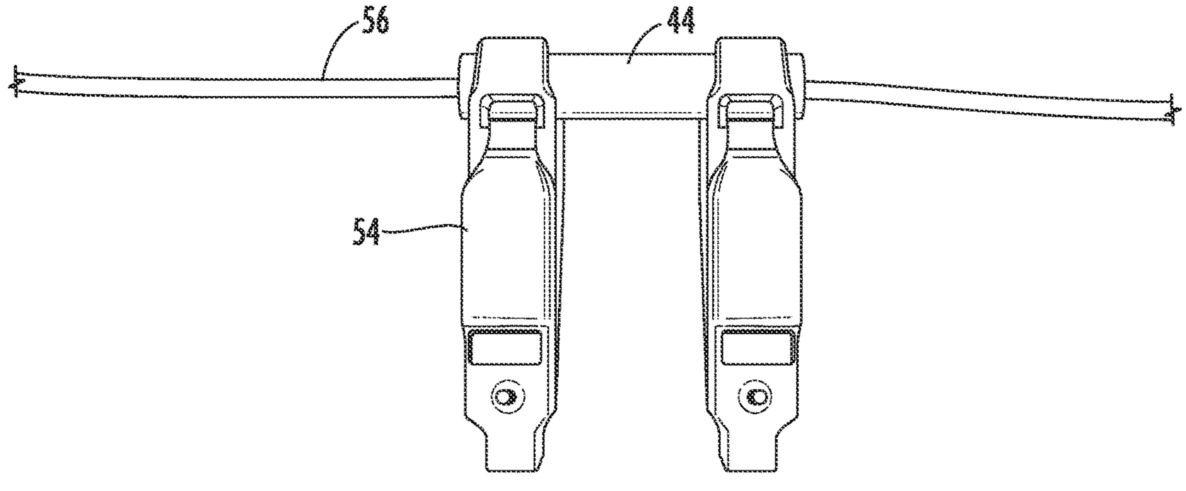
FIG. 17 is a top perspective view illustrating a polymer mold clamped in place on the outer diameter of the medical catheter.
Figure 18:
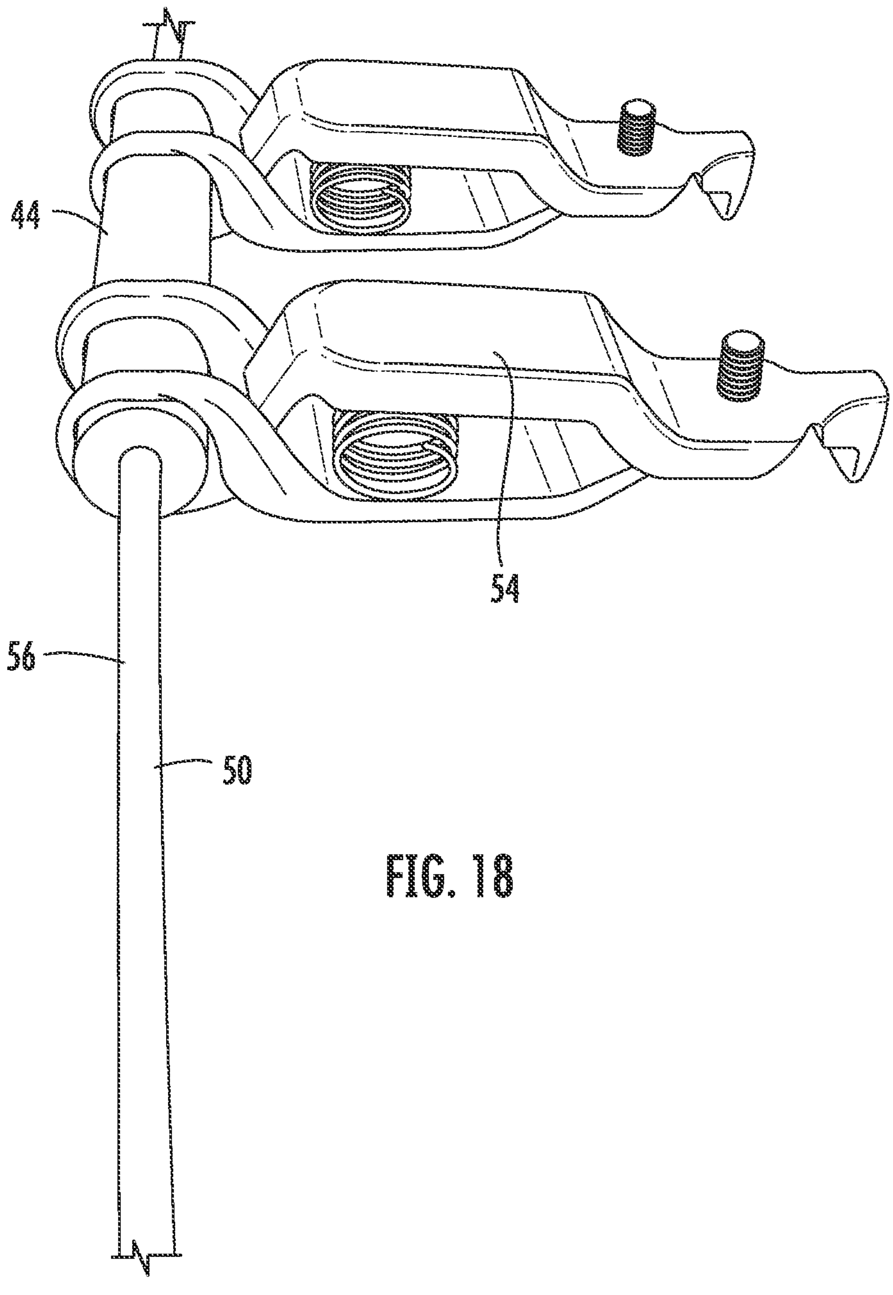
FIG. 18 is an end perspective view illustrating a polymer mold clamped in place on the outer diameter of the medical catheter.
Figure 19:
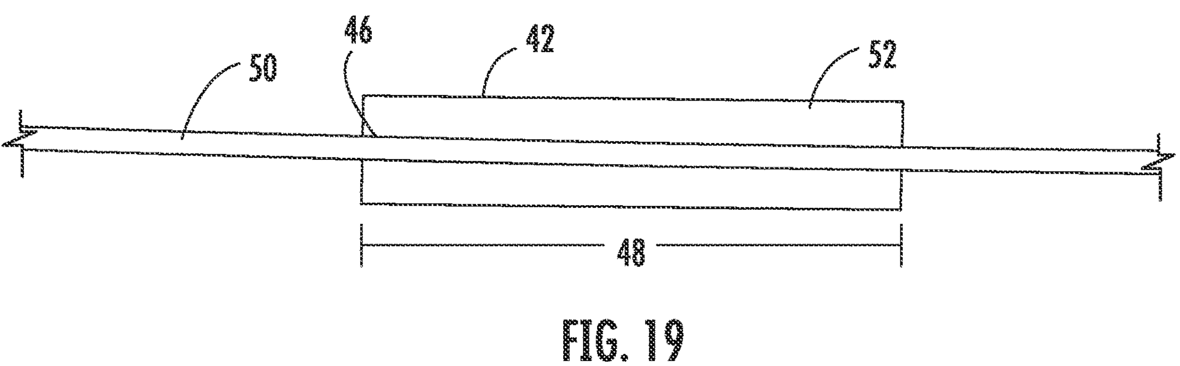
FIG. 19 is a top perspective view illustrating one half of the polymer mold having the medical catheter still positioned inside after reforming of the medical catheter sheath.
Figure 20:
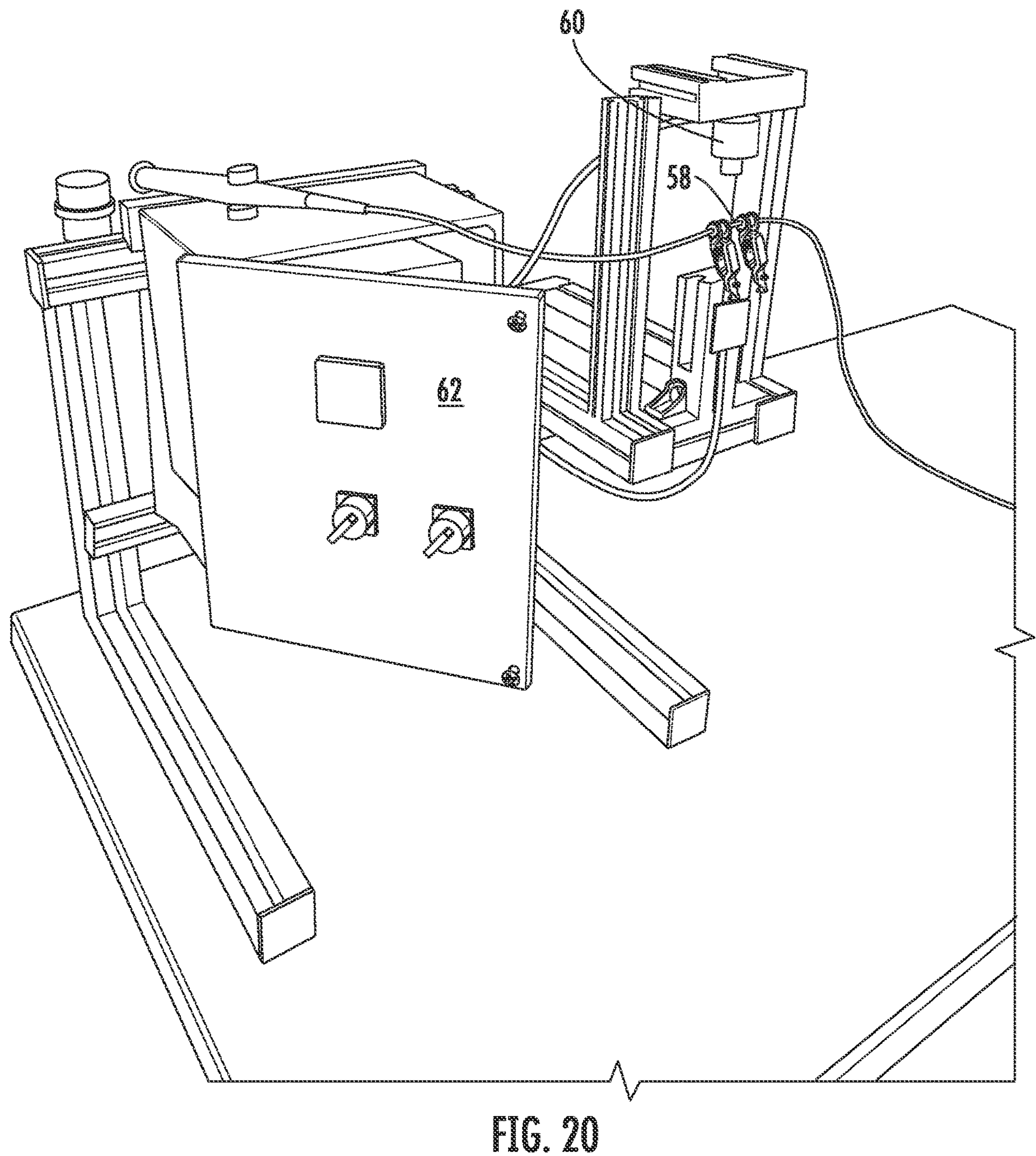
FIG. 20 is a perspective view illustrating the polymer mold positioned inside of an induction heater and cooling apparatus.
Figure 21:
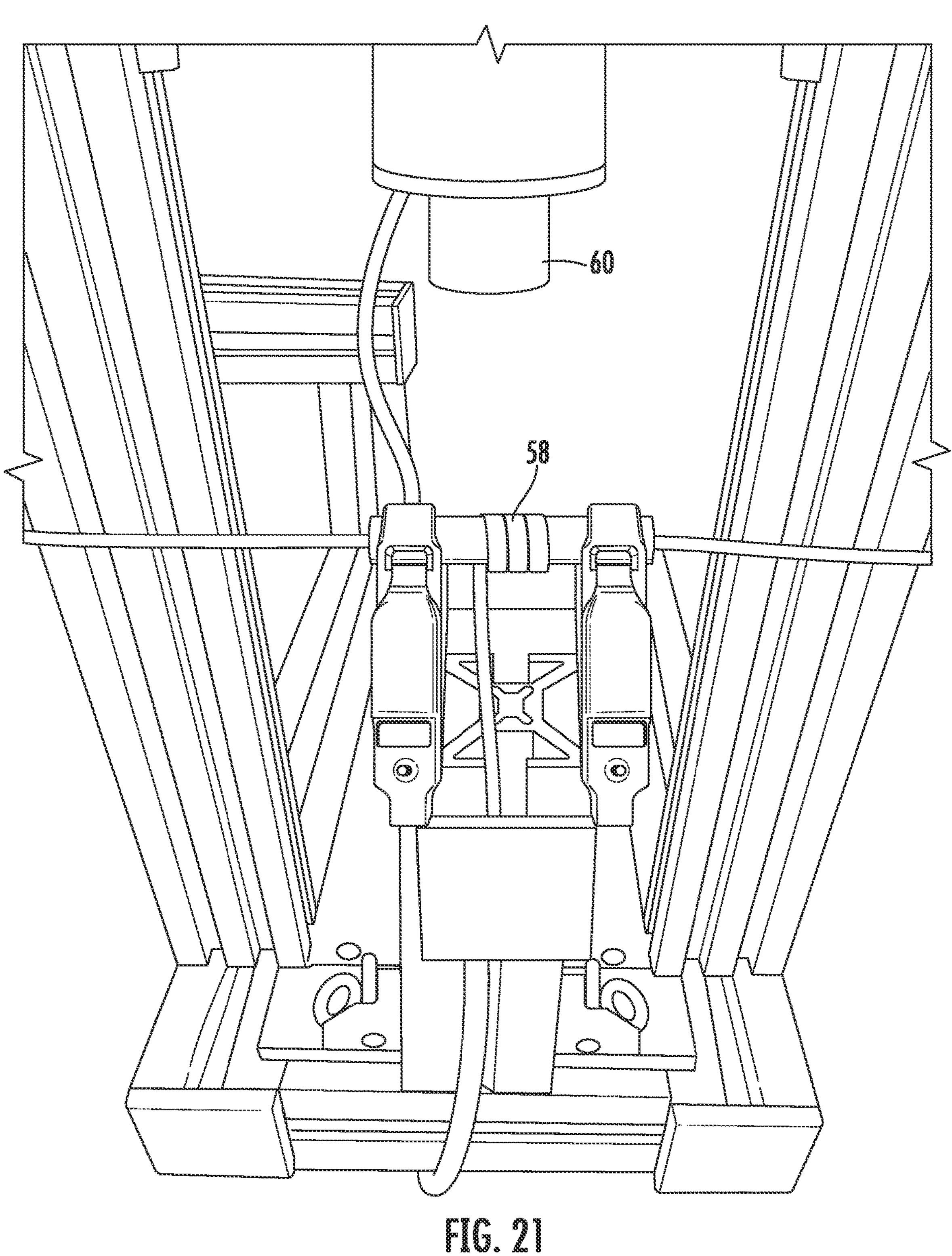
FIG. 21 is a partial close up view illustrating the polymer mold positioned inside of an induction heater and cooling apparatus.
Figure 22:
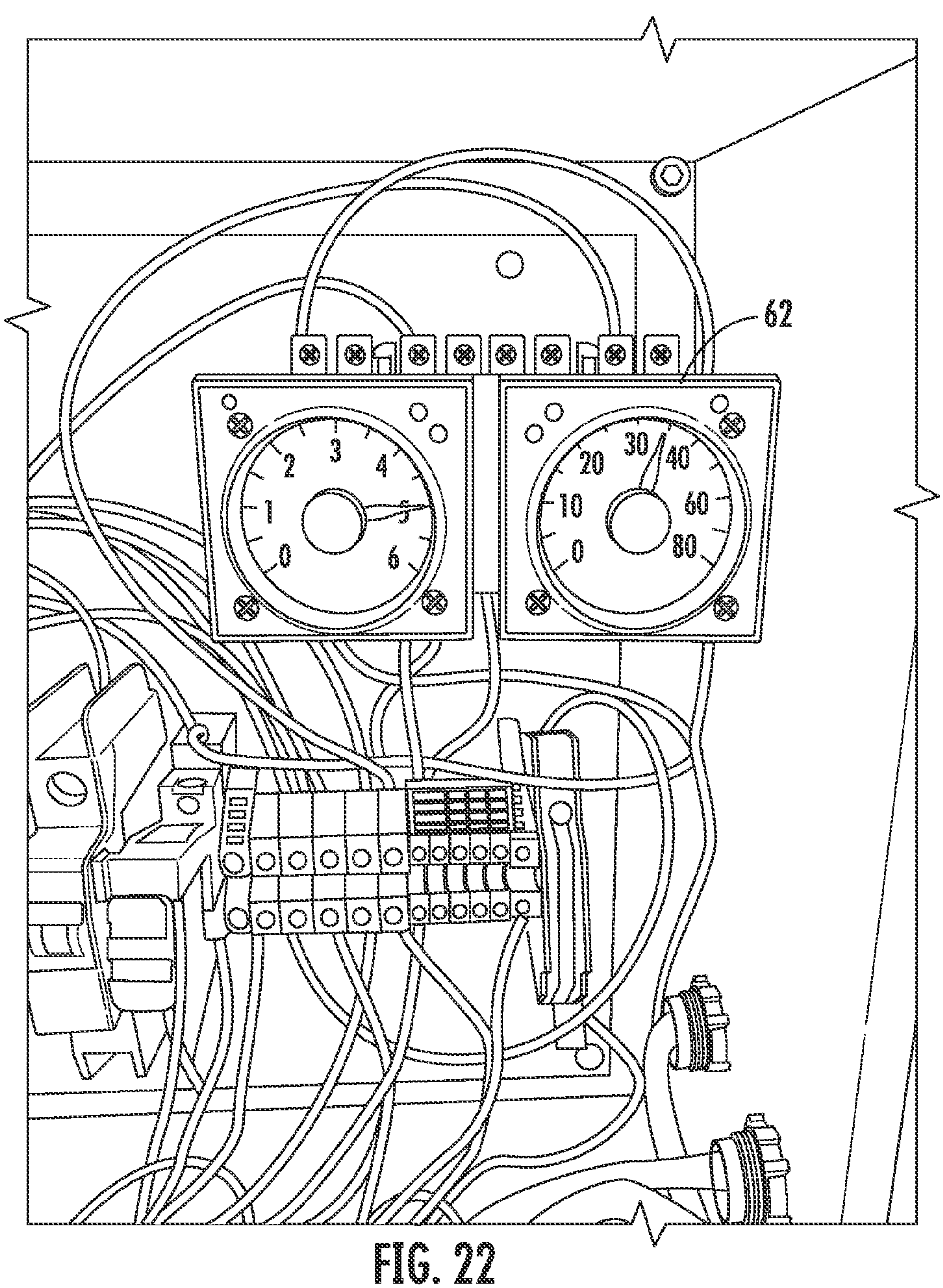
FIG. 22 is a partial close up view illustrating the controls for the induction heater and cooling apparatus.

Referring generally to FIGS. 1-22, a method and system for straightening a bent or kinked medical catheter is illustrated. The system includes a written protocol 12 for the straightening procedure for each respective catheter. The overview of the method includes parts and documents 14, equipment required 16, setup and procedure 18 and inspection 20. (FIG. 1) FIG. 2 outlines general precautions 22 for a particular catheter. In this non-limiting embodiment, the precautions are illustrated for a VNUS catheter (registered trademark) which is typically used to close veins with radio frequency ablation. It should be noted that the present system and method is suitable for use with many other catheters without departing from the scope of the invention. Referring to FIG. 3, the process flow chart 24 is illustrated. The process flow chart 24 outlines an overview of the steps required to repair the particular medical catheter. These steps may vary from one catheter to another without departing from the scope of the invention. Referring to FIG. 4, materials 26, equipment 28 and documents 30 are specified. In general, the materials 26 include a list of all the materials needed to repair a bent or kinked medical catheter. The equipment list refers to the equipment required to repair the bends and kinks of a particular medical catheter and the documents section 30 lists the documents that are needed and/or required for refurbishing a medical catheter, wherein the catheter is intended to be put back into commerce as a usable product or discarded as not usable and tracked for disposal. FIG. 5 further illustrates the process, including line clearance and documentation review 32, set up of the repair 34, and physical steps 36 for modification of the medical catheter. In general, under line clearance 32, the person repairing the medical catheter should be trained to modify the medical catheter, and they should sign off on the documents stating that they are trained. The next step under set up 34 is for the technician to determine whether the medical catheter needs kink or collar repair. Once kink or collar repair is determined, the process 12 includes a repair reference 35 that directs the technician to the required steps to complete the required work. In this particular model, the technician is given the choice of kink repair in the collar area of the medical catheter 37 and kink repair in other portions of the medical catheter 38. Under the physical steps section 36, the steps for repair of a kink in the collar section of the medical catheter are listed in order of performance. If the medical catheter requires kink repair in an area other than the collar, the technician is directed to kink repair 40, shown on FIG. 6. This section includes such steps as identifying the kinked area(s), as shown on FIGS. 9 and 10. Once the kinked area is identified, the technician is directed to clean the medical catheter 50 (FIG. 9) with alcohol or a similar film free solvent. The next step requires the technician to place the catheter in a mold 44, FIGS. 17-22. The mold is generally constructed from a high temperature resistant material such as, but not limited to, ceramic to include an outer diameter 42, an inner diameter 46, and a length 48. The mold 44 is preferably constructed to include a pair of halves 52, which may be held together with clamps 54 to enclose the outer diameter 56 of the medical catheter 50. Although not required, the mold halves 52 may include keys, pins, steps or any other alignment device without departing from the scope of the invention. Once the mold 44 is positioned around the medical catheter 50, clamps 54 may be positioned to hold the mold halves 52 in position with respect to each other and with respect to the medical catheter 50. The mold 44 and medical catheter 50 can then be positioned within a device, such as an induction coil 58, which is utilized to heat the catheter to a sufficient temperature to either activate the memory of the polymer or reform the polymer to remove the kink. Air may be provided by a blower 60 to cool the mold and catheter 50 after being heated. In this manner, the speed of cooling can be controlled, if necessary, to provide the proper material properties for the catheter 50. Once the kink(s) in the catheter 50 are repaired, the mold 44 can be removed by removing the clamps 54. FIG. 16 illustrates timer and cycle controls for the induction heater used to heat the mold 44.

Referring to FIGS. 11-16, an alternative or an additional manner of straightening kinks from a catheter 50 is illustrated. This step includes straightening rolls 64. The straightening rolls include a plurality of rollers 66 arranged in perpendicular planes with respect to each other. Each roller 66 includes a V-shaped or U-shaped groove 68 sized to accept and guide the outer diameter of the catheter. In operation, the rollers are set to bend the catheter back and forth in a decreasing manner as it passes over the rollers to cause the catheter to become straight when exiting the straightening rolls 64. The catheter 50 is thus pulled through the straightening rollers 66 at least one time to remove the kinks. Such straightening rolls are typically used for straightening solid metal wire as it is pulled from a coil for use in manufacturing. After straightening, the solid wire is typically cut to a particular length for use. After straightening the catheter 50, any other checks, such as electrical conductivity, resistance and the like may also be completed. Thereafter, the paperwork is completed regarding the inspection of the catheter. The catheter can then be cleaned and repackaged for shipment and use.

What is claimed is:

1. A method for refurbishing bent or kinked medical catheters comprising:

providing an overview of the method for refurbishing bent or kinked medical catheters including parts and documents (14), equipment required (16), setup and procedure (18) and inspection requirements (20);

supplying a process flow chart (24) outlining an overview of the steps required to repair the particular medical catheter;

wherein the equipment required (16) refers to the equipment required to repair the bends and kinks of a particular medical catheter.

2. The method for refurbishing bent or kinked medical catheters of claim 1 wherein the documents (14) lists the documents that are needed and/or required for refurbishing a medical catheter, wherein the catheter is intended to be put back into commerce as a usable product or discarded as not usable and tracked for disposal.

3. The method for refurbishing bent or kinked medical catheters of claim 2 wherein the catheter (50) is placed in a mold (44), the mold (44) being constructed from a high temperature resistant material to include an outer diameter (42), an inner diameter (46) sized to abut outer diameter of the catheter, and a length (48) sufficient to cover the bend or kink.

4. The method for refurbishing bent or kinked medical catheters (50) of claim 3 wherein the mold (44) is constructed as a split mold including two or more mold halves (52) constructed to assemble into a full loop around the catheter (50).

5. The method for refurbishing bent or kinked medical catheters (50) of claim 4 wherein the mold halves (52) include alignment keys for aligning the mold halves (52) with respect to each other.

6. The method for refurbishing bent or kinked medical catheters of claim 3, including the step of positioning the mold (44) and medical catheter (50) within an induction coil (58), the induction coil (58) being constructed and arranged to heat the catheter (50) to a sufficient temperature to activate the shape memory of the polymer forming an outer sheath of the catheter (50).

7. The method for refurbishing bent or kinked medical catheters of claim 3, including the step of positioning the mold (44) and medical catheter (50) within an induction coil (58), the induction coil (58) being constructed and arranged to heat the catheter (50) to a sufficient temperature to reform the polymer forming an outer sheath of the catheter (50).

8. The method for refurbishing bent or kinked medical catheters (50) of claim 6 including the step of controllably cooling the catheter sheath using air provided by a blower (60) after being heated to provide the desired material flexural properties for the catheter (50).

9. The method for refurbishing bent or kinked medical catheters (50) of claim 7 including the step of controllably cooling the catheter sheath using air provided by a blower (60) after being heated to provide the desired material flexural properties for the catheter (50).

10. The method for refurbishing bent or kinked medical catheters (50) of claim 3 including the step of pulling the catheter (50) through a set of straightening rolls (64), the straightening rolls (64) including a plurality of rollers (66) arranged in perpendicular planes with respect to each other, the rollers (66) each including a groove (68) sized to accept and guide the outer diameter of the catheter, the rollers (66) positioned to bend the catheter (50) back and forth in a decreasing manner as it passes over the rollers (66) to straighten the catheter (50) when exiting the straightening rolls (64).

11. The method for refurbishing bent or kinked medical catheters (50) of claim 3 including the step of checking electrical conductivity to determine if the catheter retains electrical conductivity.

* * * * *